US011132784B2

(12) United States Patent
Kesti

(10) Patent No.: US 11,132,784 B2
(45) Date of Patent: Sep. 28, 2021

(54) DETECTING MICROSCOPIC OBJECTS IN FLUIDS

(71) Applicant: UPONOR OYJ, Vantaa (FI)

(72) Inventor: Tero Kesti, Tampere (FI)

(73) Assignee: UPONOR OYJ, Vantaa (FI)

(*) Notice: Subject to any disclaimer, the term of this patent is extended or adjusted under 35 U.S.C. 154(b) by 0 days.

(21) Appl. No.: 16/770,356

(22) PCT Filed: Dec. 10, 2018

(86) PCT No.: PCT/FI2018/050896
§ 371 (c)(1),
(2) Date: Jun. 5, 2020

(87) PCT Pub. No.: WO2019/115872
PCT Pub. Date: Jun. 20, 2019

(65) Prior Publication Data
US 2020/0342584 A1  Oct. 29, 2020

(30) Foreign Application Priority Data
Dec. 11, 2017 (EP) .................................. 17206391

(51) Int. Cl.
 *G06T 7/00* (2017.01)
 *G06T 7/73* (2017.01)
 (Continued)

(52) U.S. Cl.
 CPC ....... *G06T 7/0004* (2013.01); *G01N 15/1434* (2013.01); *G01N 33/18* (2013.01);
 (Continued)

(58) Field of Classification Search
 CPC ......... G06T 7/0004; G06T 7/73; G06T 5/008; G06T 7/60; G06T 2207/10016;
 (Continued)

(56) References Cited

U.S. PATENT DOCUMENTS

2004/0169903 A1  9/2004 Kreuzer et al.
2009/0207691 A1* 8/2009 Fetvedt ................. B01F 9/10
                                                                 366/220
(Continued)

FOREIGN PATENT DOCUMENTS

GB        24321660       5/2007

OTHER PUBLICATIONS

Bahram Javidi; Enrique Tajahuerce; Pedro Andres, "Digital Holographic Microscopy: A New Imaging Technique to Quantitatively Explore Cell Dynamics with Nanometer Sensitivity," in Multi-dimensional Imaging , IEEE, 2014, pp. 197-223, doi: 10.1002/9781118705766.ch9. (Year: 2014).*

(Continued)

*Primary Examiner* — Marnie A Matt
(74) *Attorney, Agent, or Firm* — Cantor Colburn LLP

(57) ABSTRACT

A method (10) utilizes first, second, and third image data originating from first, second, and third digital image frames, respectively, captured sequentially in time of a sample volume containing a fluid possibly comprising moving microscopic objects while illuminating the sample volume by coherent light, each image data comprising, for a moving microscopic object of foreign object present in the sample volume, a hologram pattern (11); and comprises automatically generating first differential image data comprising the difference of the first and the second image data, (13a); automatically generating second differential image data comprising the difference of the second and the third image data (13b); automatically generating product of difference (POD) image data comprising the product of the first and the second differential image data, (14); and automatically detecting the presence of moving microscopic object(s) in the sample volume on the basis of product pattern(s) present in the POD image data (17).

11 Claims, 8 Drawing Sheets

(51) Int. Cl.

| | |
|---|---|
| *G01N 15/14* | (2006.01) |
| *G01N 33/18* | (2006.01) |
| *G02B 21/06* | (2006.01) |
| *G02B 21/36* | (2006.01) |
| *G03H 1/00* | (2006.01) |
| *G06T 5/00* | (2006.01) |
| *G06T 7/60* | (2017.01) |
| *H04N 5/225* | (2006.01) |
| *G01N 15/10* | (2006.01) |

(52) U.S. Cl.
CPC .......... *G02B 21/06* (2013.01); *G02B 21/367* (2013.01); *G03H 1/0005* (2013.01); *G06T 5/008* (2013.01); *G06T 7/60* (2013.01); *G06T 7/73* (2017.01); *H04N 5/2256* (2013.01); *G01N 2015/1093* (2013.01); *G01N 2015/1493* (2013.01); *G03H 2001/005* (2013.01); *G06T 2207/10016* (2013.01); *G06T 2207/10056* (2013.01); *G06T 2207/20224* (2013.01)

(58) Field of Classification Search
CPC . G06T 2207/10056; G06T 2207/20224; G06T 5/50; G01N 15/1434; G01N 33/18; G01N 2015/1093; G01N 2015/1493; G02B 21/06; G02B 21/367; G03H 1/0005; G03H 2001/005; H04N 5/2256
USPC .......................................................... 348/79
See application file for complete search history.

(56) References Cited

U.S. PATENT DOCUMENTS

| | | | | |
|---|---|---|---|---|
| 2012/0134230 | A1* | 5/2012 | Engelhardt | ........ G01N 15/1463 366/142 |
| 2017/0219999 | A1* | 8/2017 | Serabyn | ............... G03H 1/0443 |
| 2018/0231446 | A1* | 8/2018 | Svanback | ............... G01N 13/02 |

OTHER PUBLICATIONS

C. Lindensmith, J. L. Nadeau, M. Bedrossian, L. Sumrall, J. K. Wallace and E. Serabyn, "Microscopic Object Classification through Passive Motion Observations with Holographic Microscopy," 2020 IEEE Aerospace Conference, Big Sky, MT, USA, 2020, pp. 1-7, doi: 10.1109/AERO47225.2020.9172746. (Year: 2020).*

Extended European Search Report for European Patent App. No. 17206391.9 dated May 4, 2018, 6 pages.

Garcia-Sucerquia J et al: "4-D imaging of fluid flow with digital inline holographic microscopy"; Optik, Wissenschaftliche Verlag GMBH, DE; vol. 119, No. 9, Jul. 10, 2008 (Jul. 10, 2008); pp. 419-423.

Kazemzadeh Farnoud et al: "Multi spectral 1-12 digital holographic microscopy with applications in water quality assessment"; Visual Communications and Image Processing, vol. 9579; Sep. 3, 2015 (Sep. 3, 2015); pp. 957906-1 to 957906-07.

Mudanyali, Onur et al. "Detection of waterborne parasites using field-portable and cost-effective lensfree microscopy"; National Institute of Health, Lab Chip, Sep. 21, 2010; 10(18); pp. 2419-2423.

* cited by examiner

Obtaining first, second, and third image data comprising, for moving microscopic objects, hologram patterns Providing coherent light — 711

Illuminating a sample volume containing a fluid possibly comprising moving microscopic objects of foreign origin by the coherent light, whereby the microscopic objects scatter part of the light, the scattered and non-scattered light interfering so as to form interference fringes behind the microscopic objects — 712

Capturing first, second, and third digital image frames by an image sensor receiving the light propagated through the sample volume — 713

DETECTING MICROSCOPIC OBJECTS IN FLUIDS

CROSS REFERENCE TO RELATED APPLICATIONS

This application is a National Stage application of PCT/FI2018/050896, filed Dec. 10, 2018, which claims the benefit of European Application No. 17206391.9, filed Dec. 11, 2017, both of which are incorporated by reference in their entirety herein.

FIELD OF THE INVENTION

The present invention relates generally to monitoring quality of fluids, such as water. In particular, the present invention relates to methods and apparatuses for monitoring microscopic particle or microbe content of fluids by means of optical sensing.

BACKGROUND OF THE INVENTION

Water quality is an important parameter for various applications where clean water is produced, supplied, or used. Water quality may be critical as well for the safety and health of people as end users of municipal water as for various industrial processes where water having specific quality requirements is used.

Conventionally, thorough water quality analysis has been carried out as a time-consuming laboratory process where a water sample is investigated by means of analysis instruments. However, in many applications, much more rapid response time is required. Examples of such include e.g. monitoring the water quality in water treatment plants, in municipal water supply networks, or in the internal water delivery in some critical types of residential water supply systems such as those on hospitals, elderly houses, or nurseries, as well as in certain industrial processes.

In-line holography or holographic microscopy has been proposed as one potential technology for rapid water quality monitoring. In US 2004/0169903 Al, an in-line holography method for tracking particles and life forms in sea water is disclosed. In another example, compact in-line holographic microscope for detection of pathogenic waterborne parasites is disclosed in Mudanyali O, Oztoprak C, Tseng D, Erlinger A, Ozcan A. Detection of waterborne parasites using field-portable and cost-effective lensfree microscopy. *Lab on a chip.* 2010; 10(18):2419-2423. Electronic publication at www.rsc.org.

In prior art holographic microscopy methods, the reconstruction phase in which the holographic image is reconstructed, using complex mathematical algorithms, into one or more two-dimensional images of the sample, requires burdensome and time-consuming calculations and powerful, expensive computing equipment. This may hinder implementation of small-size, low-cost sensor-level implementation of in-line holographic microscopy systems.

Similarly to water quality monitoring, also various other applications exist where foreign microscope objects in a fluid need to be detected and/or analyzed.

SUMMARY OF THE INVENTION

This summary is provided to introduce a selection of concepts in a simplified form that are further described below in the Detailed Description. This Summary is not intended to identify key features or essential features of the claimed subject matter, nor is it intended to be used to limit the scope of the claimed subject matter In one aspect, a method may be implemented which may be used for detecting microscopic objects of foreign origin present in a fluid. The method may be used, for example, for monitoring water quality in water supply, distribution, or use systems and networks. The microscopic objects may be, for example, impurity particles and/or microbes. In other embodiments, instead of water, the fluid may be some other liquid or gas.

In the method, first, second, and third image data are utilized, those image data originating from first, second, and third digital image frames, respectively, captured sequentially in time by an image sensor receiving light propagated across a sample volume containing a fluid possibly comprising moving microscopic objects of foreign origin while illuminating the sample volume by coherent light, whereby the possible microscopic objects scatter part of the light, the scattered and non-scattered light interfering so as to form interference fringes behind the microscopic objects, each image data comprising, for a moving microscopic object of foreign origin present in the sample volume at the time of capture of the associated digital image frame, a hologram pattern with spatially alternating intensity formed by the interference fringes.

Further, the method comprises obtaining, possibly by automatically generating, first differential image data comprising the difference of the first and the second image data, the first differential image data comprising, for each hologram pattern present in the first or second image data, a differential pattern; obtaining, possibly by automatically generating, second differential image data comprising the difference of the second and the third image data, the second differential image data comprising, for each hologram pattern present in the second or third image data, a differential pattern; and automatically generating product of difference (POD) image data comprising the product of the first and the second differential image data, the POD image data comprising, for each hologram pattern present in the second image data, a product pattern.

Finally, the method comprises automatically detecting the presence of moving microscopic object(s) of foreign origin in the sample volume on the basis of product pattern(s) present in the POD image data.

In the method, some principles known from in-line holographic microscopy may be used.

In another aspect, an apparatus may be implemented which may be used for detecting microscopic objects of foreign origin present in a fluid, the apparatus comprising a computing arrangement configured to perform the operations of the method as defined above.

In yet another aspect, a computer program product may be implemented, comprising program code instructions which, when executed by a processor, cause the processor to perform the method as defined.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein:

FIGS. 1, 5, and 7 illustrate, as schematic flow diagrams, methods for detecting microscopic objects of foreign origin present in a fluid;

DETAILED DESCRIPTION

Figure 1:
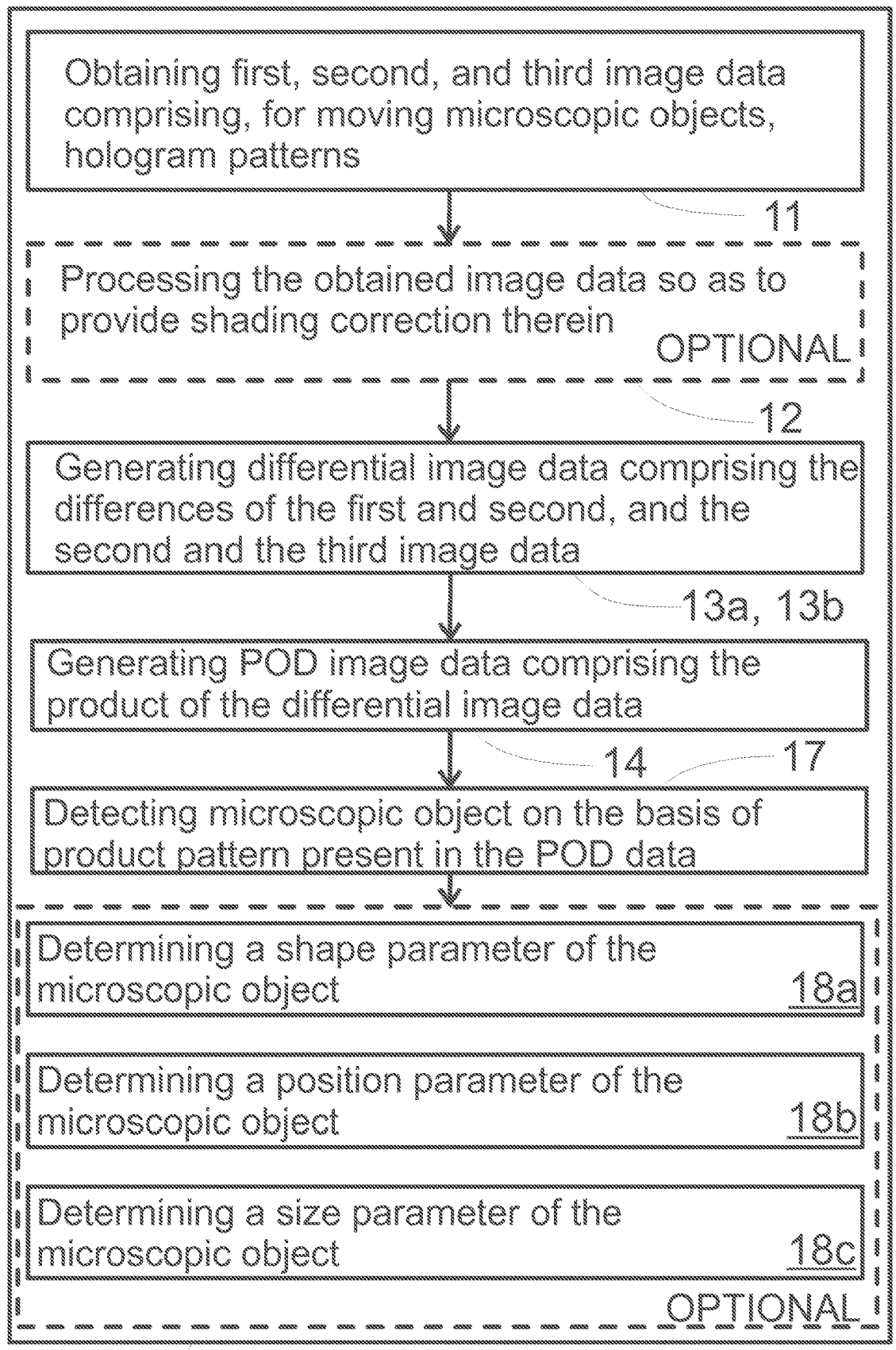

The method 10 of FIG. 1 comprises obtaining, in operation 11, first, second, and third image data originating from first, second, and third digital image frames, respectively. The first, second, and third digital image frames are such which have been captured sequentially in time by an image sensor receiving light propagated across a sample volume containing a fluid possibly comprising moving microscopic objects of foreign origin while illuminating the sample volume by coherent light.

Said obtaining the first, second, and third image data is an example of "utilizing" those image data in the method. Also the operations discussed below concerning generation of differential image data are examples of such utilization. In other embodiments, methods may be implemented where no first, second, and third image data as such are obtained, but they are utilized indirectly via obtaining and processing further image data generated on the basis of the first, second, and third image data. Such further image data may be, for example, the first and the second differential image data discussed below.

The sample volume may lie within, or be defined by, a cuvette. Being defined by a cuvette refers to the extension, i.e. the shape and the dimensions, of the sample volume being physically limited or restricted by the cuvette. Such cuvette may have any appropriate shape and structure with one or more straight or curved walls which may determine a boundary of the sample volume. Alternatively, the sample volume may comprise only a part of an inner volume defined by the cuvette.

A "digital image frame", or shortly a "frame", refers to data content initially captured via exposure of pixels or some other light-sensing element(s) of an image sensor. After capturing, a digital image frame or its image data may be processed, and new digital image frames may be formed or generated on the basis of image data of one or more initially captured digital image frames. A frame thus generally comprises image data enabling composition of a displayable digital image on the basis of that image data. Image data of a digital image frame may comprise, for example, information about light energy or intensity received by pixels of an image sensor.

"An image sensor" refers to a light sensitive component or element capable of capturing digital image frames. An image sensor may comprise, for example, a CMOS (Complementary Metal Oxide Semiconductor) or any other appropriate type of sensor element as an active, light detection imaging element.

The first, second, and third digital image frames may be captured with constant time intervals between two consequent frames. In other embodiments, there may be different time intervals between capture of different pairs of digital image frames.

A plurality of digital image frames may be captured on a continuous basis so that different sets of three digital image frames of the plurality of frames may be used as first, second, and third digital image frames. One specific digital image frame may thus be used, for example, as the first digital image frame at one time, and as the second or the third digital image frame at another time.

The expression "of foreign origin" refers to that the microscopic objects are not formed of the fluid to be investigated itself. Such objects are thus formed of materials different of the material(s) of the fluid itself so that the objects are carried within or by the fluid. They may originate, for example, from the materials of pipes or containers in which the fluid at issue is conveyed or stored. Microscopic particles of the materials of such systems may be released to the fluid, for example, in result of a pipe breakage or equipment failure. Alternatively, microscopic objects of foreign origin may originate from foreign bodies or contaminants ended up within such pipes or containers. In the case of water supply systems, for example, such foreign body producing microbes into the fluid may be a dead animal.

In the case of water supply, distribution, or use systems and networks, microbes not normally present may be, for example, various bacteria, such as bacteria belonging to coliform or *Legionella* groups, protozoa such as *Giardia lamblia*, or various types of algae.

On the other hand, from the physical properties point of view, microscopic objects of foreign origin have typically, for example, a refractive index differing from that of the fluid. This enables detection of such objects by means of optical sensing. In the method of FIG. 1, this is utilized in that the detection of the microscopic objects is based on scattering of light by the microscopic objects due to the difference between the refractive indices of the microscopic objects and the fluid.

"Moving" nature of a microscopic object refers to a non-stationary object, thus an object changing its position between capture of two consequent digital image frames.

When illuminating the sample volume by the coherent light, the possible microscopic objects therein scatter part of the light, and the scattered and non-scattered portions of the illuminating light may interfere so as to form interference fringes behind the microscopic objects.

Illuminating by coherent light refers to at least part of the light by which the sample volume is illuminated being spatially and temporally sufficiently coherent so that said interference is possible. Thus, "illuminating by coherent light" does not exclude the possibility of illuminating the sample volume at the same time also by non-coherent light. Thus, light by which the sample volume is illuminated may comprise coherent and non-coherent light.

"Behind" refers to the locations of the interference fringes as observed from the direction of incidence of the illuminating light, i.e. the coherent light by which the sample volume is illuminated. In other words, when observed from the location of a light source producing the coherent illumination light, the interference fringes are formed mainly behind the microscopic objects, i.e. at the side of the microscopic objects opposite to the side from which the coherent light is incident on the microscopic objects.

In consequence, each of the first, second, and third image data comprises, for a moving microscopic object present in the sample volume at the time of capture of the associated digital image frame, a hologram pattern with spatially alternating intensity formed by the interference fringes.

The coherent light, i.e. the illuminating light, may be emitted or guided into an expanding cone or beam or into a collimated beam. In the former case, the interference fringes are expanded as function of the distance from the scattering microscopic objects. Further, irrespective of whether the illuminating light is emitted or guided into an expanding or into a collimated light beam, the interference fringes expand due to the scattering of the light into various directions, depending on the types of the microscopic objects and the wavelength of the illuminating light. Consequently, the longer the distance between a microscopic object and the image sensor, the larger is the hologram pattern formed on the image sensor.

From dimensional point of view, "microscopic" objects refer to objects having their characteristic dimensions, such as maximum diameter, length, or width, in the range of 0.1, 0.5 or 1.0 to 50 or 100 µm. Objects with so small characteristic dimensions are not visible to human eye, so they cannot be detected visually. On the other hand, holograms formed by that sized objects are detectable by image sensor having a reasonably small size. Further, with such micrometer scale characteristic dimensions, objects scatter light mainly forward, thereby enabling efficient detection by in-line holography.

The first, second, and third image data may comprise initial image data directly defined by the captured digital image frame. In other embodiments, those image data may be generated by first preparing or processing such initial image data in some appropriate way. Such preparation or processing may be carried out beforehand or as a part of the method.

As an example of such preparation or processing, the method of FIG. 1 comprises an optional operation 12 where the first, second, and third image data are automatically processed so as to provide shading correction therein.

Shading correction refers to equalizing the overall brightness or background intensity over the image area. Non-uniform overall brightness or background intensity may result, for example, from non-uniform illumination intensity, non-uniform sensitivity of the image sensor, or some dirt on the optical surfaces on the optical path between the illuminating light source and the image sensor.

Shading correction results in the overall brightness or background illumination being uniform and normalized throughout the image area so that the mean intensity of the image frame is 1. This being the case for each of the first, second, and third digital image frame means that also possible frame to frame fluctuation or variation of the overall brightness or background intensity variation is eliminated. On the other hand, shading correction preserves local intensity variations in the digital image frame.

Many approaches are basically known in the art to carry out shading correction for a digital image frame. For example, reference image data may be utilized which is generated as a mean of several test images captured without any sample in the sample volume.

Optionality of the shading correction operation 12 refers to that other embodiments may be implemented without processing the image data so as to provide shading correction. That may be the case, for example, if the overall brightnesses or background intensities are already substantially uniform and the mean intensities of the obtained image data are already normalized so as to be 1.

"Obtaining" image data originating from a digital image frame refers to any appropriate way of providing available, for automatic data processing and/or storage purposes, such data content. Ready-generated first, second, and third image data may be stored in any appropriate memory in an apparatus or device carrying out the method or in some other apparatus or device or, for example, in a cloud server. Such ready-generated data content may be obtained in the method using any appropriate, wired or wireless data or signal transmission path. In some embodiments, said "obtaining" may also comprise generating the image data or processing initial image data so as to produce the prepared image data. An example of this is illustrated in FIG. 7.

With the first, second, and third image data obtained, the method 10 of FIG. 1 comprises, in operation 13a, automatically generating first differential image data comprising the difference of the first and the second image data. A differential image data may be considered as image data of an artificial differential digital image frame. In the example of FIG. 1, said generating the first differential image data is an example of "obtaining" such image data. In other embodiments, methods may be implemented where ready-generated first differential image data is obtained.

The difference of the first and the second image data refers to differential image data generated via subtraction of the intensity values of the second image data from the intensity values of the first image data, or vice versa.

In result of such subtraction, the first differential image data comprises, for each such hologram pattern which is present in the first or in the second image data, thus only in one of them, a differential pattern. Depending on whether a hologram pattern is present in the first or in the second image data, the associated differential pattern corresponds to the original hologram pattern or the inversion thereof, respectively.

If the first and the second image data are shading corrected with the mean intensities thereof being 1, the first differential image has zero man intensity. Then, the first differential image data may comprise the original or inverted hologram patterns of the first and the second image data, and substantially zero intensity (possibly with some noise) elsewhere.

In operation 13b corresponding to the operation 13a above, the method comprises automatically generating second differential image data comprising the difference of the second and the third image data. In the example of FIG. 1, said generating the second differential image data is an example of "obtaining" such image data. In other embodiments, methods may be implemented where ready-generated second differential image data is obtained.

What is discussed above concerning the first differential image data and the generation thereof applies, mutatis mutandis, also to the second differential image data and the generation thereof.

In result of such subtraction, the second differential image data comprises, for each such hologram pattern which is present in the second or in the third image data, thus only in one of them, a differential pattern. Depending on whether a hologram pattern is present in the second or in the third image data, the associated differential pattern corresponds to the original hologram pattern or the inversion thereof, respectively.

In this specification, the term "hologram pattern" is basically used as referring to patterns formed by interference fringes caused by moving objects present in the sample only. Also a stationary microscopic object present in the sample volume or generally lying between the illuminating light source and the digital image sensor causes a hologram pattern in the image data of a captured digital image frame. However, such hologram pattern caused by a stationary object appear similarly in each of the first, second, and third image data and is therefore absent from the first and the second differential image data resulting from the subtraction. Thereby, hologram patterns caused e.g. by a dirt or dust particle adhered onto surfaces of the apparatus or device are automatically cleaned from the differential images and do not disturb the detection of moving microscopic particles.

Each hologram pattern present in the first or in the third image data appears, in its original form or as an inverted pattern, in one of the first and the second differential image data only. Instead, those hologram patterns present in the second image data have their counterparts in both of the first and the second differential image data. In one of them such counterpart in the form of a differential pattern corresponds to the original hologram pattern. In the other one, there is a differential pattern corresponding to an inversion of the original hologram pattern.

The spatially alternating intensity of the original hologram patterns is basically preserved, although it may be inverted as discussed above, in the differential patterns resulting in the differential image data.

In operation 14, product of difference (POD) image data is automatically generated, the POD image data comprising the product of the first and the second differential image data. The POD image data may be considered as image data of an artificial POD digital image frame.

The product of the first and the differential image data refers to product image data generated via multiplying the intensity values of the first differential image data and the second differential image data by each other.

In result of such multiplication, the POD image data comprises a product pattern for each such hologram pattern which is present in the second image data and therefore has a counterpart in both of the first and the second differential image data.

Due to the multiplication of the first and the second differential image data, the product patterns have high absolute intensity values which may be substantially equal to the second power of the intensity values of the original hologram pattern. Such high intensity values provide a good basis for the operation 17 where the presence of one or more moving microscopic object of foreign origin in the sample volume is detected on the basis of one or more product patterns present in the POD image data.

Detecting the presence of a microscopic object "on the basis of" a product pattern present in the POD image data refers to interpreting the presence of a product pattern in the POD image data as an indication of a moving microscopic object of foreign origin present in the sample volume. Then, the detection may be carried out directly on the basis of the product pattern. In other words, the presence of such object may be detected from the POD image data.

Detecting the presence of microscopic objects refers, first, to determining whether there are any microscopic objects in the fluid. In this sense, detecting the presence of such objects may also comprise determining and concluding that there is no such object present in the fluid volume through which the illuminating light propagated to the image sensor. On the other hand, when there is a plurality of product patterns in the POD image data, the method may naturally comprise, in addition to determine the general presence of the microscopic objects, also the number of them in the analyzed fluid volume.

The result of the detection operation, i.e. the information about the presence of at least one microscopic object in the analyzed fluid volume, may be arranged in any appropriate electric data or signal form suitable for storage or transmitting further.

"Automatically" performing one or more operations of the method refers to performing the operation(s) at issue, for example, said detection of the presence of the microscopic object(s) in the fluid, partially or completely automatically by means of one or more appropriate data processing units or modules.

Performing an operation completely automatically refers to carrying out the operation according to predetermined rules and procedures, without need for any contribution provided or determination performed by a user of an apparatus or device incorporating such unit or module. In performing an operation partially automatically, some contribution may be provided or determination may be performed by a user of an apparatus or device incorporating such unit or module. In addition to those operations specifically stated to be performed automatically, also other operations may be carried completely or partially automatically.

Many advantageous effects may be achievable by the above method. First, determining the presence of microscopic objects in the fluid directly on the basis of the POD image data requires relatively low computing or data processing power, especially in comparison to conventional holographic microscopy where a true reconstruction, at one or more two-dimensional planes of the three-dimensional sample volume, is calculated, and the detection of the scattering objects is carried out on the basis of the reconstructed image(s). On the other hand, the detection of microscopic objects may be carried out substantially faster than in the approach utilizing full reconstruction of the sample volume or two-dimensional sections thereof.

Savings in the required computational power and/or processing time may enable implementation of small-size, low-cost detection apparatuses for on-line operation, for example, for water quality monitoring.

Further, in the method described above, possible hologram patterns resulting from stationary objects such as dirt or dust particles possibly adhered onto various device surfaces are automatically cleaned away from the data on the basis of which the detection of moving microscopic objects is carried out.

Figure 2:
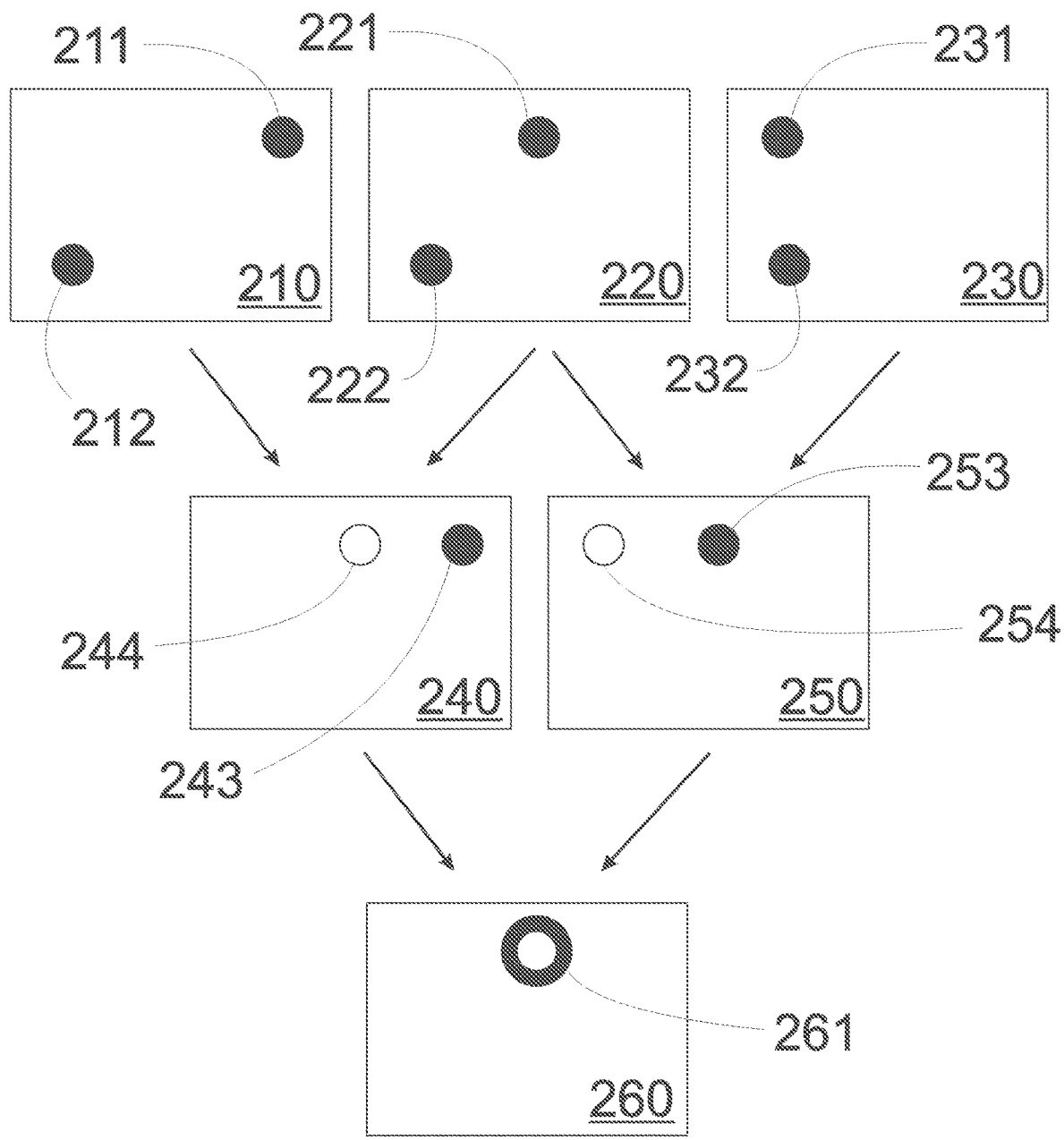
FIGS. 2 and 6 illustrate schematically digital image frames and their image data usable in methods for detecting microscopic objects.

The process illustrated in FIG. 2 by means of digital image frames may be basically in accordance with the method described above with reference to FIG. 1.

In the process of FIG. 2, sequentially captured first, second, and third digital image frames 210, 220, 230 are illustrated. In the example of FIG. 2, as illustrated in the digital image frames, each image data comprises one hologram pattern 211, 221, 231 originating from a moving microscopic object present in the sample volume at the time of capture of the digital image frame at issue. The hologram patterns of the different image frames may originate from one single moving microscopic object propagating in the sample volume and thus appearing at different locations at the times of capture of the different digital image frames. Alternatively, they may originate from different microscopic objects.

Further, each image data also comprises a hologram pattern 212, 222, 232 originating from a stationary microscopic object which may be e.g. dust or dirt.

These hologram patterns appear in the digital image frames and the image data thereof substantially similarly, and at the same location in the image area. Consequently, as illustrated in the first and second differential digital image frames 240, 250, they are substantially removed from the first and second differential image data.

In the first differential image data 240, there are two differential patterns. A first differential pattern 243 of the first differential image data originates from the hologram pattern 211 present in the first image data 210. A second differential pattern 244 of the first differential image data originates from the hologram pattern 221 present in the second image data 220. The first differential pattern 243 appears substantially similarly to the hologram pattern 211 of the first image data 210. Instead, the second differential pattern 244 appears substantially as an inverted pattern of the hologram pattern 221 of the second image data 220. This is due to the formation of the first differential image data 240 on the basis of subtraction of the second image data 220 from the first image data 210.

Also in the second differential image data 250, there are two differential patterns. A first differential pattern 253 of the second differential image data originates from the hologram pattern 221 present in the second image data 220. A second differential pattern 254 of the second differential image data originates from the hologram pattern 231 present in the third image data 230. The first differential pattern 253 appears substantially similarly to the hologram pattern 221 of the second image data 220. Instead, the second differential pattern 254 appears substantially as an inverted pattern of the hologram pattern 231 of the third image data 230. This is due to the formation of the second differential image data 250 on the basis of subtraction of the third image data 230 from the second image data 220.

In other embodiments, the subtraction of the image data for generating the differential image data may be carried out the other way round. A first differential image data may be based on subtraction of the first image data from the second image data, and a second differential image data may be based on subtraction of the second image data from the third image data.

The artificial POD digital image frame 260 and the image data thereof is generated on the basis of multiplying the first and the second differential image data by each other.

In the POD image data, there is one product pattern 261 originating from the multiplication of the second differential pattern 244 of the first differential image data 240 and the first differential pattern 253 of the second differential image data 250 by each other. Due to the inverted nature of the second differential pattern 244 of the first differential image data 240, the multiplication results in inverted nature or form of the product pattern 261. In the case of shading corrected first, second, and third image data 210, 220, 230, the mean intensities of the first and the second differential image data 240, 250, are zero. Then, said inverted nature or form means that those intensity values originating from the non-zero intensity values of the intensity fringes associated with the hologram pattern 221 present in the second image data 220 are negative.

The presence of the product pattern 261 in the POD image data indicates the presence of the moving microscopic object in the sample volume at the time of capture of the second image data. Thereby, detection of the microscopic object may be based on detection of the product pattern in POD image data.

POD data initially generated on the basis of product of a first and a second differential image data may be further processed or prepared so as to facilitate the detection of possible product patterns. For example, as the intensity values of a product pattern may be negative, POD image data may be automatically inverted so that the negative intensity values thereof becomes positive, and vice versa. Thereafter, possible resulting negative values, which may be caused, for example, by positive values of noise signal in the original POD image data, may be automatically converted to zero. In another embodiment, all negative intensity values of the original POD signal may be automatically converted into their absolute values. In both cases, the resulting processed or "inverted" POD image data may be such that the product patterns thereof comprise positive (or zero) intensity values only.

Further, such inverted POD data may be further processed, for example, by smoothing the typically spatially alternating intensity of the product pattern(s).

"Smoothing" refers here to decreasing the variation of the spatially alternating intensity of the image data at least in the area of a product pattern. Any appropriate filter(s) and algorithm(s) may be utilized to achieve this purpose. In result, the filtered POD image data may comprise, in the area of the product pattern, intensity which alternates spatially only slightly.

Such possibly filtered POD image data may be further processed by thresholding locally increased intensity by automatically setting values thereof exceeding a predetermined threshold level to a specific constant intensity level, while converting the values remaining below said threshold value to zero, or to the possibly non-zero base level. Thereby, the filtered image data may comprise the filtered hologram pattern as a binary image. Alternatively, the values exceeding the threshold level may be left unchanged.

From an image point of view, converting the initially negative values of the spatially alternating intensity into their positive counterparts, possibly followed by the smoothing and/or the thresholding, may result in filtered image data where the processed POD image data comprises "blobs" at the locations of the initial product patterns. A "blob" refers to an area with substantially constant or only slightly spatially alternating, locally increased intensity.

Figure 3:
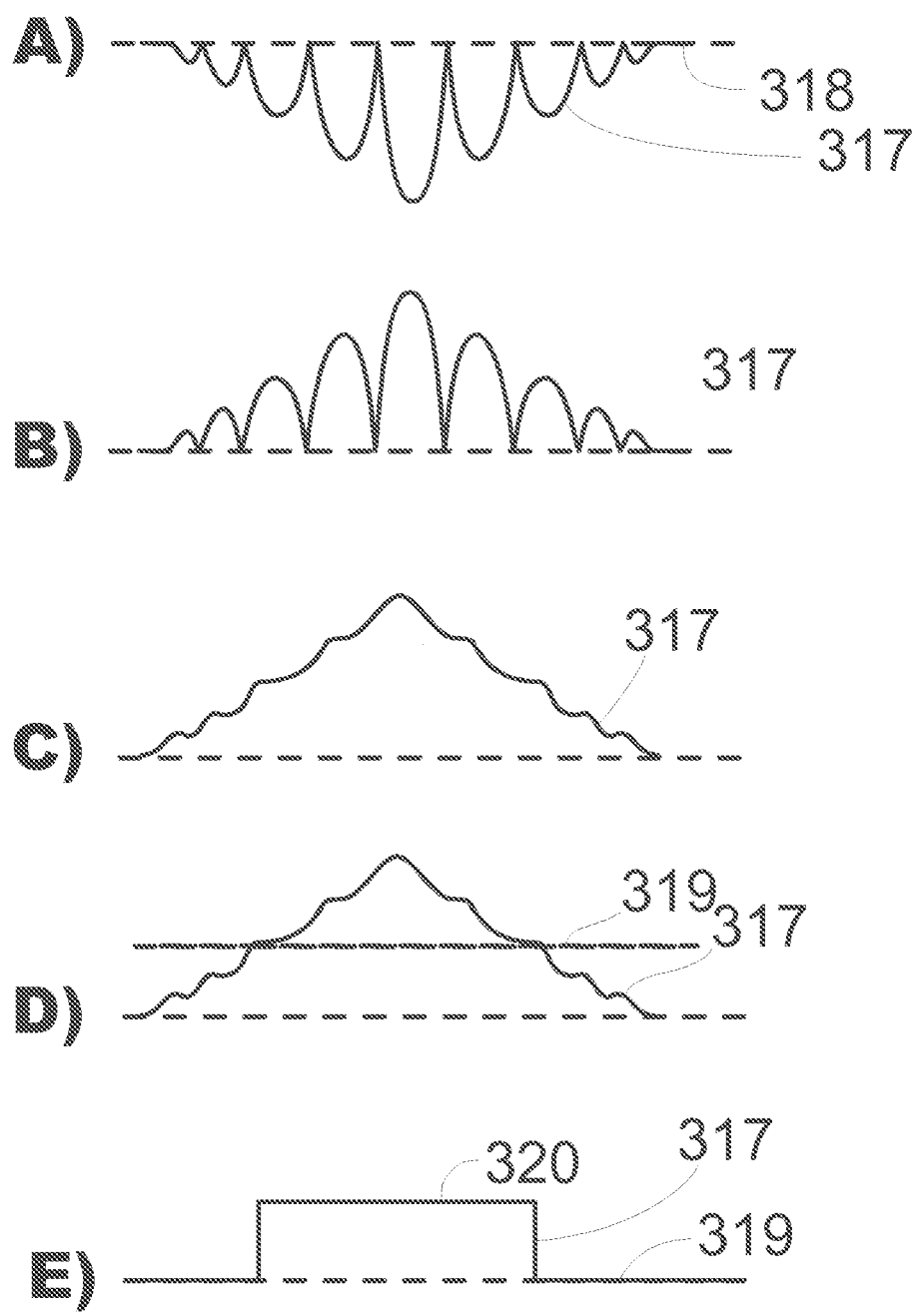
FIG. 3 illustrates schematically intensity of image data.

Optional operations of converting the negative intensity component values positive, smoothing the thereby achieved intensity component curve, and further thresholding the smoothened curve are illustrated in FIG. 3.

In graph 3 A) spatially alternating intensity 317 of a product pattern present in POD image data is summoned to a mean intensity level 318 which may be zero. The alternating intensity, resulting from multiplying a differential pattern and an inversion thereof, has merely negative intensity peaks.

In graph 3 B), the spatially alternating intensity 317 is illustrated after converting the initially negative values of the filtered spatially alternating intensity component into their positive counterparts.

In the next phase, illustrated in graph 3 C), the intensity curve 317 has been smoothed, resulting in intensity values in the area of the product pattern slightly alternating as an envelope curve of the original inverted intensity peaks.

In graph 3 D), a predetermined intensity threshold level 319 is illustrated as marked on the intensity curve 317.

Finally, graph 3 E) illustrates the intensity signal 317 in the processed POD image data at the location of the original product pattern after a thresholding operation. In a thresholding operation, the values of the intensity component exceeding the threshold level have been converted into a constant top level 320, whereas those values remaining below the threshold level 319 have been set to zero.

Figure 4:
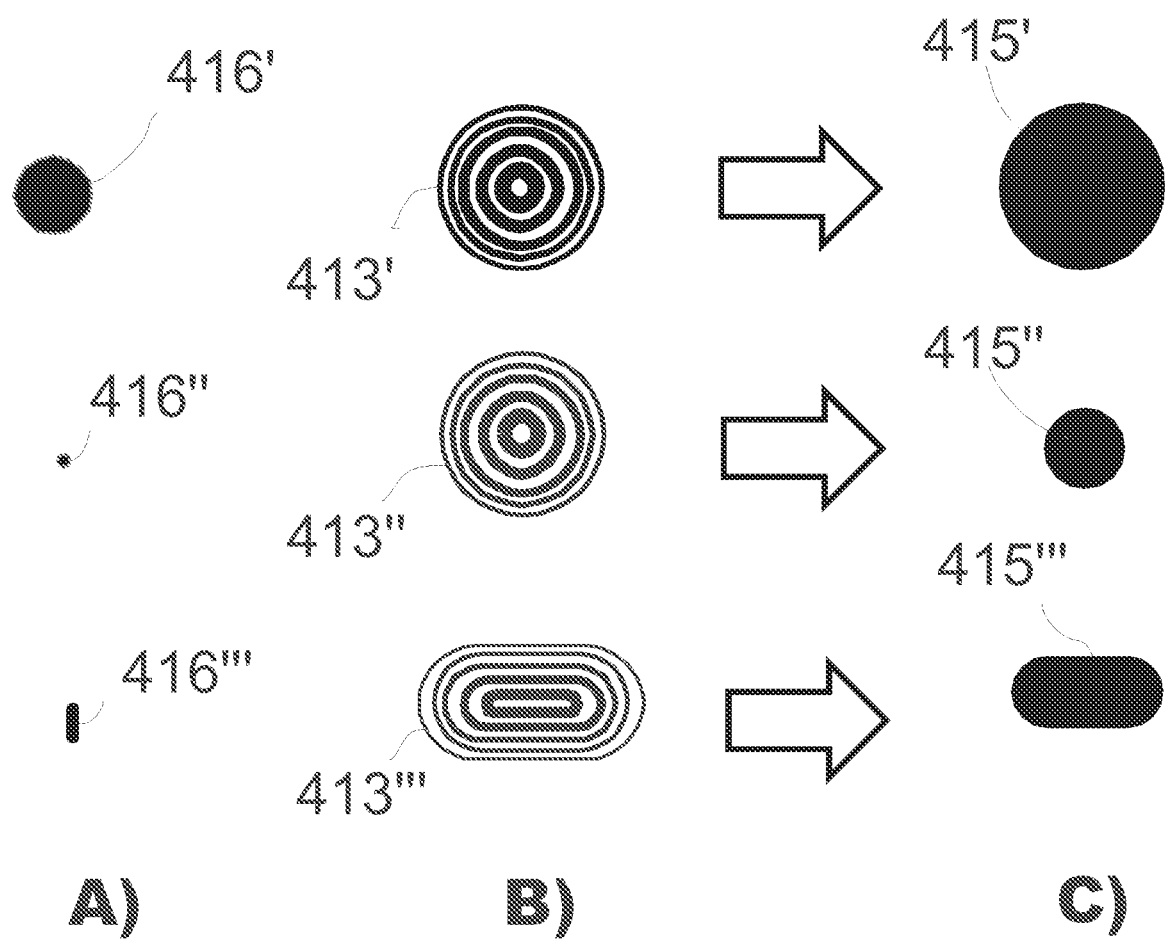
FIG. 4 illustrates schematically microscopic objects and hologram patterns produced thereby.

FIG. 4 illustrates relationship between real moving microscopic foreign objects present in a sample volume at the time of capture of a second digital image frame, and product patterns resulting therefrom in POD image data.

In drawing 4 A), two substantially point-like or round microscopic objects 416', 416" with different sizes, and one elongated microscopic object 416''', are shown. Drawing 4

B) illustrates schematically two round and one slightly elongated initial product patterns 413', 413", 413''', respectively, originating from the differential patterns in first and second differential image data. The product patterns are formed by concentric interference fringes. Although not visible in the drawings, the bigger the microscopic object is the brighter the interference fringes of the associated prepared hologram pattern are.

Drawing 4 C) illustrates processed product patterns 415', 415", 415''' resulting from the initial product patterns after processing the POD image data by operations similar to those illustrated in FIG. 3. In result of converting the negative values of the filtered spatially alternating intensity component into their positive counterparts, followed by smoothing and thresholding operations, the processed product patterns of the filtered image data are plain blobs. The shapes of the blobs indicate the shape of the microscopic object, and the sizes thereof depend on the brightnesses of the prepared hologram patterns, and therefore on the sizes of the microscopic objects.

To detect product patterns in the POD image data, any appropriate pattern recognition filter(s) or algorithm(s) may be used. For example, in the case of filtered hologram data with filtered hologram patterns comprising "blobs" as discussed above, various blob detecting filters and algorithms are known and may be used.

With one or more product patterns detected in a POD image data, possible further analysis of the image data can be focused on, or limited to, the actual locations of the product patterns in the image area. Great savings in the required computing power may then be saved because the rest of the image data does not need to be analyzed.

Further, the sizes of the hologram patterns may remain substantially unchanged during the process of generating the differential and POD image data, as well as during possible further processing of the POD image data. Hologram patterns are typically substantially larger than the actual objects, so in the above method, the noise possibly present in the image data may be not as detrimental as in the case of detecting the smaller size objects in a reconstructed image.

Referring back to FIG. 1, the method 10 comprises a further optional operation 18a, where at least one shape parameter of a detected microscopic object of foreign origin is automatically determined on the basis of shape of the associated product pattern present in the POD image data or shape of the associated differential pattern present in the first or second differential image data. "Shape" of a product pattern or differential pattern may refer to the shape of the contour of the pattern, but also, or alternatively, to the overall intensity distribution within the pattern.

"A shape parameter" refers to any appropriate indicator depending on or indicating one or more features of the shape of the microscopic object.

Determination of a shape parameter may be based on predetermined relationship between the probable shapes of the microscopic objects and the associated shapes of the differential patterns and/or the product patterns. For example, an elongated object such as some particular bacteria types, typically produces a slightly elongated hologram pattern, i.e. a hologram pattern with the interference fringes stronger in one direction than in the direction orthogonal to that direction. This shape may be mainly remained during generation of the differential and POD image data and possible further processing of the POD image data, allowing straightforward determination of a shape parameter of the original microscopic object on the basis of the differential and/or product patterns.

In determining the shape parameter of a microscopic object, any appropriate pattern recognition algorithm(s) may be used.

Another optional operation 18b may be carried out irrespective of whether any of the previous optional operations discussed above are also carried out. In that operation, the method may further comprise automatically determining at least one position parameter of a detected microscopic object on the basis of position of the associated product pattern in the POD image data or position of the associated differential pattern present in the first or second differential image data, respectively.

"A position parameter" refers to any appropriate indicator depending on or indicating one or more characteristic features of the position of the microscopic object in the differential and/or POD image data. With the geometry of the sample volume, illumination, and the image sensor known, the position parameter(s) may be used to further determine a position parameter of the detected microscopic object in the sample volume at the time of capture of the second digital image frame.

As yet another optional operation 18c, the method may further comprise automatically identifying, for a product pattern present in the POD image data, associated differential pattern present in the first or the second differential image data, and automatically determining at least one size parameter of the associated microscopic object on the basis of amplitude of the spatially alternating intensity of the associated differential pattern. Thus, after detection of a product pattern, e.g. via detection of a "blob" in processed POD image data and thus a microscopic object of foreign origin, it may be evaluated, i.e. identified, which differential patterns present in the differential image data produced that particular product hologram pattern. Size parameter(s) indicating the size of the associated microscopic object which produced the differential patterns may then be determined on the basis the amplitude of the prepared hologram pattern at issue.

"A size parameter" refers to any appropriate indicator depending on or indicating one or more characteristic features, such as diameter or length, of the associated microscopic object.

Alternatively, it may be possible to determine one or more size parameters of the detected microscopic object directly on the basis of the product pattern present in the POD image data, which may have been first further processed by appropriate operations, assuming the product pattern has sufficient intensity amplitude information of the original hologram pattern left. In yet another approach, one or more size parameters may be determined on the basis of the original hologram pattern present in the second image data.

"Amplitude" used in determining the size parameter(s) may refer to the amplitude of a spatially up and down alternating intensity component, possibly summoned to a spatially substantially constant or slowly changing base level. The amplitude of such intensity component, used in determining the size parameter(s) may be, for example, maximum or average peak or peak to peak amplitude, second largest peak or peak to peak amplitude, or any other appropriate amplitude related property of the intensity in the area of the hologram pattern, the differential pattern, or the product pattern.

In those embodiments comprising determining one or more size parameters of the microscopic object, the correlation between the brightness of the interference fringes and the object size is utilized. The larger the object is, the higher the intensity is in the interference maxima of the interference fringes.

The optional operations of the method illustrated in FIG. 1 may be carried out irrespectively of each other. Thus, method may be implemented with any combination of one or more optional operations. Apart from the shading correction which is to be carried out before generating the differential image data, the optional operation(s) may be carried out in any appropriate order, or at least partially simultaneously.

Any of the shape, position, and size parameters may be provided for further use or for storage as any appropriate electric data or signal form.

Further, in addition to the amplitude or brightness, also other parameters such as the spatial frequency of the interference fringes may be utilized in determining a size parameter of the microscopic object.

Identifying the differential pattern associated with a specific product pattern may be based on comparison of the positions of the product pattern and the differential pattern in the POD image data and the differential image data, respectively.

There may be some non-zero noise or noise-like intensity signal left in a differential image in areas outside the differential pattern(s). When multiplying the first and the second differential image data by each other, such non-zero amplitude values may result in non-zero spatially alternating intensity pattern(s) in the POD image data at the location(s) of possible differential pattern(s) originating from hologram patterns present in first or third image data only.

Figure 5:
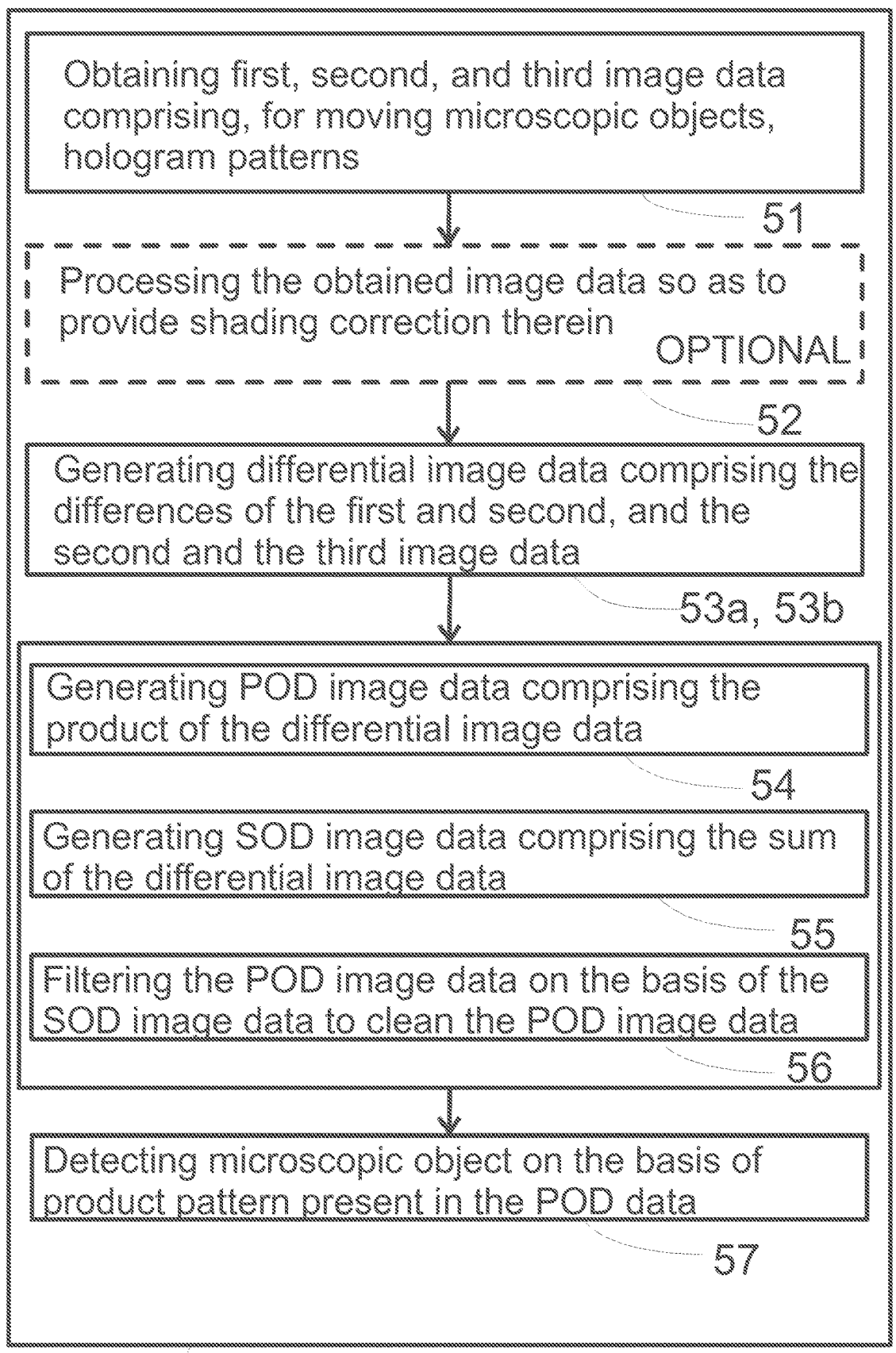

The example illustrated in FIG. 5 may facilitate cleaning such possible spatially alternating intensity, not related to a true product pattern, out of the POD image data.

Up to generating first and second differential image data in operation 53a, 53b, the method 50 of FIG. 5 may be carried out in accordance with any of the methods discussed above with reference to FIGS. 1 to 4.

The method 50 of FIG. 5 distinguishes from those discussed above with reference to FIGS. 1 to 4 in that it comprises, before detecting the presence of moving microscopic object(s) of foreign origin, in operation 55, automatically generating sum of difference (SOD) image data which comprises the sum of the first and the second differential image data. The operation 55 of generating the SOD image data may be carried out before, after, or simultaneously with the generation of the POD image data.

As discussed above, in POD image data, there are actual product patterns for the first differential patterns only which appear at the same locations in the first and the second differential image data. Differently from this, in summing the first and the second differential image data for the SOD image data, such first differential patterns being inversions of each other substantially vanish. Instead, possible second patterns each appearing in one of the first and the third image data only remain during the summing operation. Therefore, the SOD image data comprises a sum pattern for each such hologram pattern which is present in the first or in the third image data only.

Further differently from the methods discussed above with reference to FIG. 1, the method 50 of FIG. 5 comprises, in operation 56, automatically filtering the POD image data on the basis of the SOD image data so as to set the absolute values of the spatially alternating intensity of the POD image data at the location of a possible sum pattern present in the SOD image data below or at a limit value. Such limit value may be, for example, zero.

"Filtering" refers to any appropriate procedure enabling said adjustment of the POD image data at the locations of possible sum patterns present in the SOD image data. In such filtering, for example, the SOD image data may be used as a "mask" so that at the location(s) of sum pattern(s) thereof, the spatial alternation of the intensity of the POD image data is removed.

Figure 6:
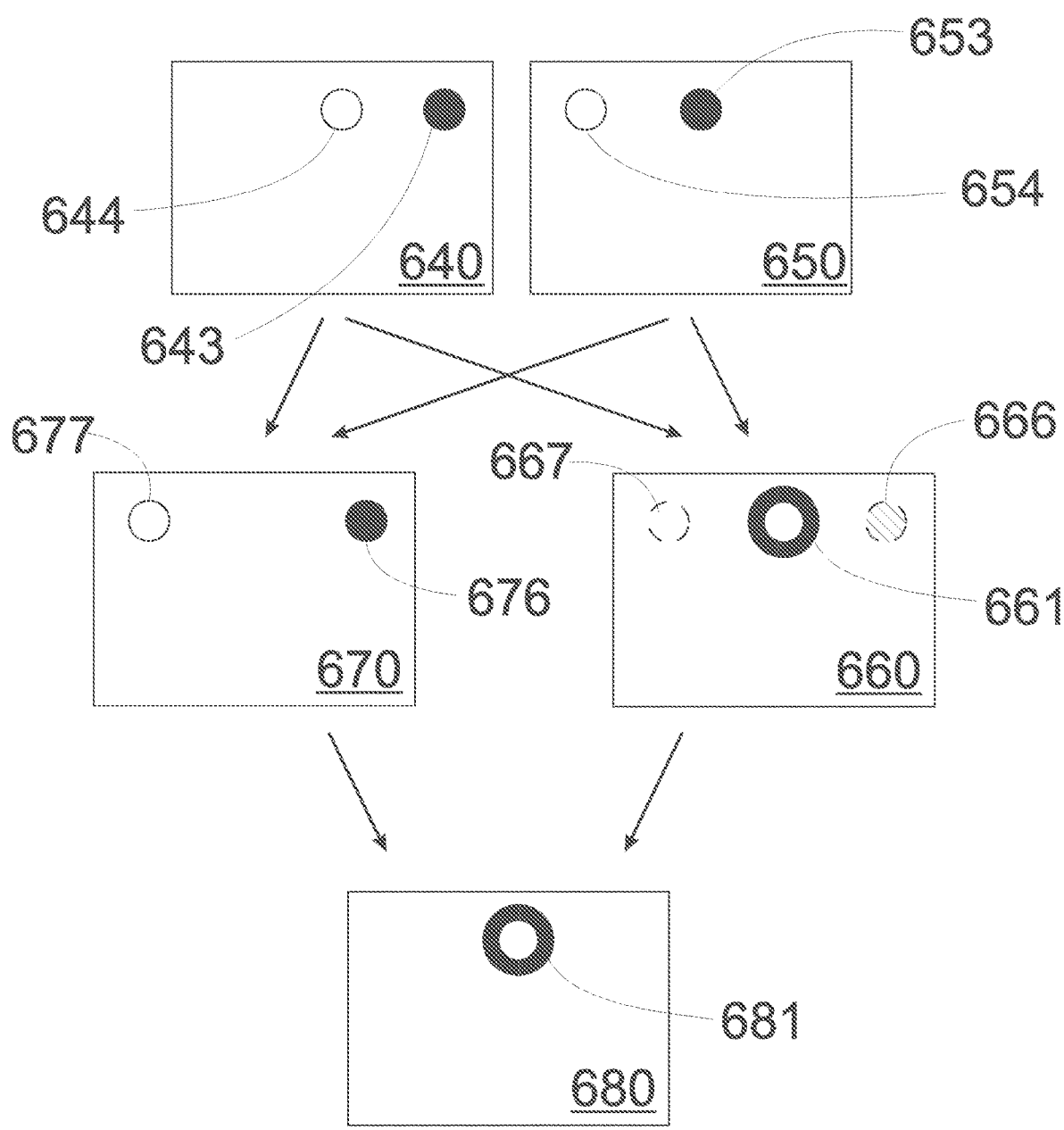

Such generation of SOD image data and its utilization in "cleaning" POD image is illustrated in FIG. 6. The first and second differential image data 640, 650 of FIG. 6 may be in accordance with the first and the second differential image data discussed above with reference to FIG. 2. The initial POD image data 660 generated on the basis of the first and the second differential image data differs from the POD image data of FIG. 2 in that it comprises first and second spatially alternating intensity patterns 666, 667 at the locations of the first differential pattern 643 of the first differential image data 640 and the second differential pattern 654 of the second differential image data 650, respectively.

In the SOD image data 670, there is a first sum pattern 676 originating from the first differential pattern 643 of the first differential image data 640, and a second sum patter 677 originating from the second differential pattern 654 of the second differential image data 650.

Filtering the POD image data by means of the SOD image data as described above results in filtered POD image data 680. In the filtered POD image data 680, the product pattern 681 is still present but the spatially alternating intensity patterns 666, 667 of the initial POD image data 660 have been "cleaned" away.

Referring back to FIG. 5, in operation 57, the presence of one or more moving microscopic object of foreign origin in the sample volume is automatically detected on the basis of one or more product patterns present in the filtered POD image data.

The methods discussed above and the embodiments thereof may be implemented as sampling processes where a stationary sample volume of a fluid is contained in a closed cuvette, the cuvette structure possibly defining the sample volume.

Alternatively, in some applications, microscopic objects present or borne in flowing fluid may be detected and possibly the properties thereof determined.

In the above, the method is discussed with the focus on the actual data processing operations only. This indicates that the preceding phase of capturing the image data is not necessarily part of the method. This allows, for example, implementation of analysis devices or apparatuses which carry out the detection and determination of the microscopic objects separately from the actual illumination and image capture operations.

It is also possible to implement a complete detection method comprising those operations also. The method 70 partially illustrated in FIG. 7, which may be basically in accordance with any of the previous embodiments, represents an example of this.

In the method 70 of FIG. 7, obtaining the first, second, and third image data in operation 71 comprises providing, in sub-operation 711, coherent light; and illuminating, in sub-operation 712, a sample volume which may lie within, or be defined by, a cuvette, and contains a fluid possibly comprising moving microscopic objects of foreign origin by the coherent light. Upon the illumination, the microscopic objects scatter part of the light and the scattered and non-scattered light interfering so as to form interference fringes behind the microscopic objects. In sub-operation 713, the first, second, and third digital image frames are captured by an image sensor receiving the light propagated across the sample volume.

In this embodiment, the method thus comprises also the actual illuminating and image capturing operations required to generate the prepared image data.

The first, second, and third image data of the captured first, second, and third digital image frames, respectively, may form as such the first, second, and third image data. Alternatively, those image data may be generated or produced by processing said image data by any appropriate operation(s).

As discussed above, the above methods and various embodiments thereof can be used, for example, for monitoring quality of a fluid, such as water or industrial process fluids where microscopic particle or microbe content of the fluid is an important parameter indicating the quality of the fluid. Then, in addition to detecting microscopic objects, the methods and their embodiments discussed above may further comprise initiating predetermined actions if the microscopic object content, i.e. the amount and/or type of detected microscope objects, meet predetermined criteria.

Such actions may comprise, for example, collecting a sample of the monitored fluid for further analysis, controlling a process or system in which the monitored fluid is contained or from which it is supplied, and/or generating an alarm signal.

The operations of the methods and the various embodiments thereof explained above as being carried out at least partially automatically may be carried out by means of any suitable computing and/or data processing means. Such means may comprise e.g. at least one processor and at least one memory coupled to the processor. The at least one memory may store program code instructions which, when run on the at least one processor, cause the processor to perform operations according to various operations of the method. Alternatively, or in addition, at least some of those operations may be carried out, at least partially, by means of some hardware logic elements or components, such as Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc., without being limited to those examples.

What is stated above about the details, ways of implementation, preferred features, and advantages with reference to the method aspect apply, mutatis mutandis, also to the apparatus aspect discussed hereinafter. The same applies vice versa.

Figure 8:
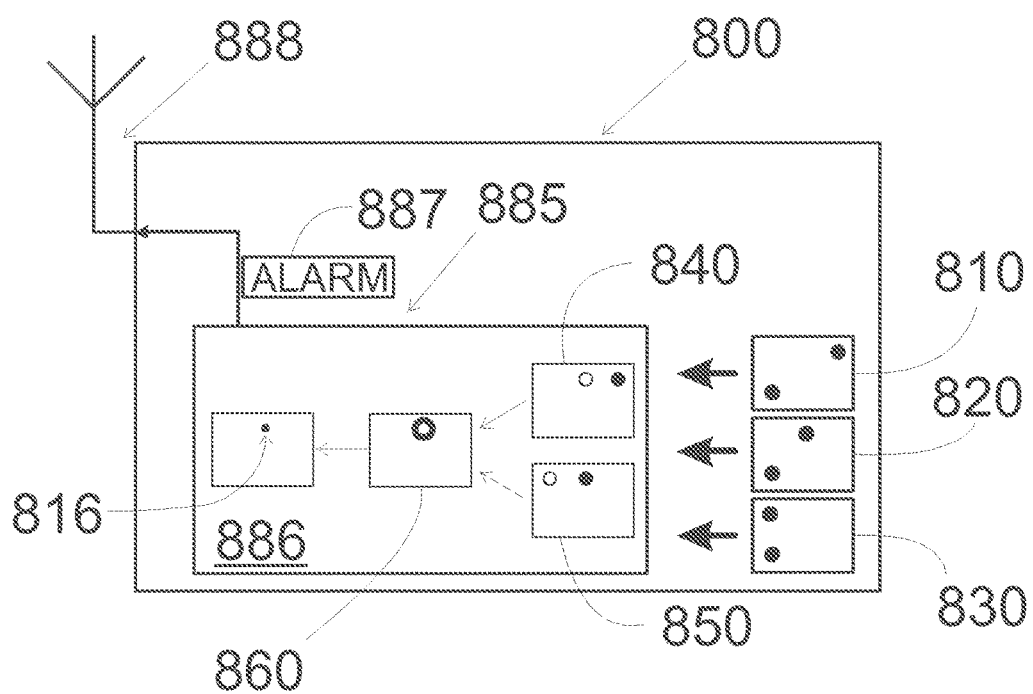
FIGS. 8 and 9 illustrate apparatuses for detecting microscopic objects of foreign origin present in a fluid.

The apparatus 800 of FIG. 8 may be used for detecting microscopic objects of foreign origin present in a fluid. The apparatus comprises a computing arrangement 885 configured to perform the operations of any of the methods discussed above with reference to FIGS. 1 to 6.

The computing arrangement may comprise any appropriate data processing and communicating equipment, unit(s), element(s), and component(s) capable of carrying out the operations of the method discussed above.

In the example of FIG. 8, the computing arrangement 885 comprises a processing unit 886 configured to carry out the operations of obtaining the first, second, and third image data 810, 820, 830; and automatically generating the first and the second differential image data 840, 850 and the POD image data 860. In other embodiments, a processing unit may be configured to obtain ready-generated first and second differential image data instead of generating such. Then, there is no need to obtain the first, second, and third image data as such. The processing unit 886 may be further configured to automatically generate possible SOD data (not illustrated in FIG. 8) and carry out possible filtering of the POD image data. Finally, the processing unit 886 is configured to automatically carry out the detection of the presence of moving microscopic object(s) 816 of foreign origin in the sample volume from the (possibly filtered) POD image data.

The processing unit may further be configured to carry out any of the optional operations discussed above.

A computing arrangement or processing unit thereof "configured to" perform a specific method operation means that the computing arrangement or processing unit comprises, or serves as, "means for" performing that operation.

The computing arrangement may comprise separate means for different operations. Alternatively, any of such means for performing those various operations specified above may be combined so that more than one operation is carried out by the same means. It is even possible that all those operations are carried out by the same means, e.g. by a single data processing module or unit. In the example of FIG. 8, this is illustrated by the processing unit 886.

Any means for performing any of the above operations may comprise one or more computer or other computing and/or data processing components, units, devices, or apparatuses. In addition to actual computing and/or data processing means, the means for performing said operations may naturally also comprise any appropriate data or signal communication and connecting means, as well as memory or storage means for storing generated and/or received data.

Computing and/or data processing means, such as the processing unit 886 of the example of FIG. 8, serving as means for performing one or more of the above operations may comprise, for example, at least one memory and at least one processor coupled with the at least one memory. Then, the at least one memory may comprise computer-readable program code instructions which, when executed by the at least one processor, cause the apparatus to perform the operation(s) at issue.

In addition to, or instead of, a combination of a processor, a memory, and program code instructions executable by the processor, means for performing one or more operations may comprise some hardware logic components, elements, or units, such as those examples mentioned above in the context of the method aspect.

In addition to actual detection of microscopic objects in the fluid to be analyzed, computing arrangement 885, in practice the processing unit 886 thereof, is configured to generate an alarm signal 887 indicating that a predetermined criteria for microscopic particle amount, type, or, for example, average size, are met. The apparatus comprises transmitting arrangement 888 to transmit such alarm signal from the apparatus, for example, to some centralized control system. The transmitting arrangement may comprise, for example, wireless data communication means including, for example, an antenna. The transmitting arrangement and the operation of generating an alarm signal are optional features, and embodiments without those features are also possible. In other embodiments, computing arrangements may be implemented which are not configured to generate any alarm signal. Then, the apparatus may be implemented without any transmitting arrangement.

In the above, the apparatus is defined as comprising the computational or data processing means only. In an embodiment illustrated in FIG. 9, which may be in accordance with any of the previous embodiments discussed above with reference to FIG. 8, a complete detecting apparatus 900 is implemented. The detecting apparatus 900 differs from that of FIG. 8 in that it comprises, in addition to the computing arrangement 985, also a measurement arrangement 990 configured to carry out capturing of the first, second, and third image data 910, 920, 930 to be processed by the computing arrangement. Thus, in this approach, the apparatus also comprises means for performing the measurements of the physical quantity.

In more detail, the measurement arrangement comprises a cuvette 991 defining a sample volume for receiving a fluid 992 possibly containing microscopic objects 916 of foreign origin; an illuminating arrangement 993 configured to emit coherent light 994 and illuminate the fluid received in the sample volume by the coherent light, whereby the possible microscopic objects scatter part of the light, the scattered and non-scattered light interfering so as to form interference fringes behind the microscopic objects; and an image sensor 995 positioned and configured to capture digital image frames by receiving the light propagated across the cuvette and the sample volume therein.

In this embodiment, the computing arrangement 985 is connected to the measurement arrangement 990 to receive image data of the captured digital image frame(s) which form the basis for the first, second, and third image data 910, 920, 930 discussed above. The computing arrangement may also be configured to control the measurement arrangement, and the illuminating arrangement and the image sensor thereof.

A "cuvette" refers to any appropriate sample cell or container capable of receiving the fluid to be analyzed. A cuvette may comprise one or more walls defining an inner volume thereof for receiving said fluid. Defining the inner volume means that the one or more walls limit or surround a cross-section of the inner volume throughout a perimeter thereof. In other words, the one or more walls and/or some other appropriate structure of the cuvette completely encircles the entire inner volume at least at one cross-section thereof, thereby preventing escaping of the fluid to be measured from the inner volume in directions in the plane of such cross-section.

A cuvette and a measuring arrangement as a whole, incorporating the cuvette, may have any appropriate dimensions, taking into account the application at issue. For example, the thickness of the inner volume in the direction of incidence of the illuminating light may be, for example, in the range of 0.5 to 1 mm. The width of the cuvette may be adjusted, for example, on the basis of the size of the light sensitive cell of the image sensor which may lie, for example, at a distance of about 1 to 3 mm from the inner volume of the cuvette. For example, the cuvette may have, in one or more directions, a width of 4 to 8 mm. One pixel of the light sensitive cell may have a width, for example, in the range of 1.5 to 5 µm. For example, the width of a rectangular pixel may be about 2 µm. The positioning of the light source of the illuminating arrangement may vary depending on, for example, on the light source and the size of the light emitting surface thereof. In an example, a laser diode as a light emitting element of a light source may be positioned at some tens of millimeters, for example about 40 mm, from the inner volume of the cuvette.

Figure 9:
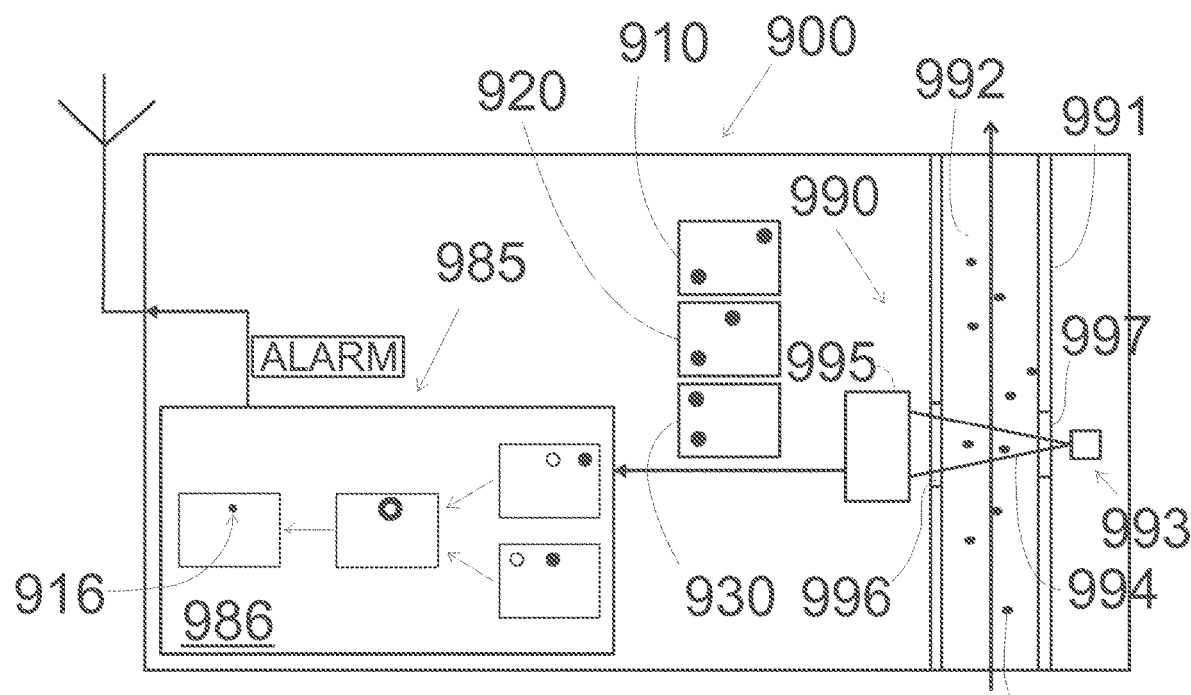

In general, a cuvette may be of sampling type, wherein a discrete volume may be stored in the cuvette. In the example of FIG. 9, it is of a flow-through type, wherein continuous flow of the fluid 992 to be analyzed may be led through the cuvette during the analysis. In other embodiments, other types of cuvettes may be used. For example, in some embodiments, a cuvette may be configured to serve alternatively as a sampling type cuvette or as a flow-through cuvette.

The cuvette 991 comprises windows 996, 997 allowing the illuminating light emitted by the illuminating arrangement to enter and exit the cuvette. In the example of FIG. 9, the illuminating arrangement and the image sensor are positioned at opposite sides of the cuvette to form a direct propagation path of light from the illuminating arrangement to the image sensor via the cuvette.

The illuminating arrangement 993 may comprise any appropriate light source, such as a laser diode, capable of producing coherent light. The light may have wavelength(s), for example, in the range of 350 to 500 nm, without being limited to that range. The illuminating arrangement may further comprise any appropriate optical elements configured to guide the emitted coherent light towards the cuvette and the sample volume to illuminate the fluid received therein.

The image sensor 995 may be of any appropriate type. For example, it may comprise a CMOS (Complementary Metal Oxide Semiconductor) or CCD (Charge-Coupled Device) cell. The image sensor may be a black and white type sensor. Suitable size of the active area and the resolution of the image sensor depend on the overall configuration of the measurement arrangement. In some applications, it may have, for example, a size of 5×5 mm$^2$. In some applications, the active area of the image sensor may have, for example, 5 million pixels.

The apparatuses of FIGS. 8 and 9 may be implemented as stand-alone apparatuses or sensors. Alternatively, they may form a part of a larger controlling or monitoring system.

In the examples of FIGS. 8 and 9, the apparatuses are illustrated as one-piece devices. In other embodiments, apparatuses or systems may be implemented which comprise multiple parts or modules connected appropriately, e.g. via wired or wireless data transfer connections, to each other. Then, one apparatus or system part or module may be configured to carry out part of the method only. For example, it may be possible to have the operations of obtaining the differential image data carried out in different part or module than the operations of generating of the POD (and possible SOD) image data and detecting the presence of microscopic object(s).

In yet another aspect not illustrated in the drawings, a computer program product may be implemented comprising program code instructions which, when executed by a processor, cause the processor to perform the operations discussed above with reference to method aspect or any embodiment thereof.

Such computer program product may be stored on any appropriate computer-readable medium; computer referring here to any type of automatic computing means.

It is to be noted that the present invention is not limited to the embodiments and examples above.

Instead, the embodiments of the present invention can freely vary within the scope of the claims.

It will be understood that the benefits and advantages described above may relate to one embodiment or example or may relate to several embodiments or examples. The embodiments and examples are not limited to those that solve any or all of the stated problems or those that have any or all of the stated benefits and advantages. It will further be understood that reference to 'an' item refers to one or more of those items.

The term "comprising" is used in this specification to mean including the feature(s) or act(s) followed thereafter, without excluding the presence of one or more additional features or acts.

The invention claimed is:

1. A method (10) for detecting microscopic objects of foreign origin present in a fluid by utilizing first, second, and third image data originating from first, second, and third digital image frames, respectively, captured sequentially in time by an image sensor receiving light propagated across a sample volume containing a fluid to be analyzed for moving microscopic objects of foreign origin while illuminating the sample volume by coherent light, whereby the possible microscopic objects scatter part of the light, the scattered and non-scattered light interfering so as to form interference fringes behind the microscopic objects, each image data comprising, for a moving microscopic object of foreign origin present in the sample volume at the time of capture of the associated digital image frame, a hologram pattern with spatially alternating intensity formed by the interference fringes (11), the method comprising:
obtaining first differential image data comprising the difference of the first and the second image data, the first differential image data comprising, for each hologram pattern present in the first or second image data, a differential pattern (13*a*);
obtaining second differential image data comprising the difference of the second and the third image data, the second differential image data comprising, for each hologram pattern present in the second or third image data, a differential pattern (13*b*);
automatically generating product of difference (POD) image data comprising the product of the first and the second differential image data, the POD image data comprising, for each hologram pattern present in the second image data, a product pattern (14); and
automatically detecting the presence of moving microscopic object(s) of foreign origin in the sample volume on the basis of product pattern(s) present in the POD image data (17).

2. A method (10) as defined in claim 1, comprising automatically processing the first, second, and third digital image frames so as to provide shading correction therein (12).

3. A method as defined in claim 1, further comprising automatically determining at least one shape parameter of a detected microscopic object of foreign origin on the basis of shape of the associated product pattern present in the POD image data or shape of the associated differential pattern present in the first or second differential image data, respectively (18*a*).

4. A method as defined in claim 1, further comprising automatically determining at least one position parameter of a detected microscopic object on the basis of position of the associated product pattern in the POD image data or position of the associated differential pattern present in the first or second differential image data, respectively (18*b*).

5. A method as defined in claim 1, further comprising automatically identifying, for a product pattern present in the POD image data, an associated differential pattern present in the first or the second differential image data, and automatically determining at least one size parameter of the associated microscopic object of foreign origin on the basis of amplitude of the spatially alternating intensity of the associated differential pattern (18*c*).

6. A method (50) as defined in claim 1, further comprising, before detecting the presence of moving microscopic object(s) of foreign origin:
automatically generating sum of difference (SOD) image data comprising the sum of the first and the second differential image data, the SOD image data comprising, for each hologram pattern present in the first or the third image data, a sum pattern (55); and
automatically filtering the POD image data on the basis of the SOD image data so as to set the absolute value of the spatially alternating intensity of the POD image data at the location of a possible sum pattern present in the SOD image data below or at a limit value (56).

7. A method (70) as defined in claim 1, wherein the method comprises obtaining the first, second, and third image data (71), said obtaining comprising:
providing coherent light (711);
illuminating a sample volume containing a fluid possibly comprising moving microscopic objects of foreign origin by the coherent light, whereby the possible microscopic objects scatter part of the light, the scattered and non-scattered light interfering so as to form interference fringes behind the microscopic objects (712); and
capturing the first, second, and third digital image frames by an image sensor receiving the light propagated across the sample volume (713).

8. An apparatus (800) for detecting microscopic objects (816) of foreign origin present in a fluid, the apparatus comprising a computing arrangement (885) configured to perform the operations of the method as defined in claim 1.

9. An apparatus (900) as defined in claim 8, further comprising measurement arrangement (990) comprising:
a cuvette (991) defining a sample volume for receiving a fluid (992) possibly comprising moving microscopic objects (916) of foreign origin;
an illuminating arrangement (993) configured to emit coherent light (994) and illuminate fluid received in the sample volume by the coherent light, whereby the possible microscopic objects (916) scatter part of the light, the scattered and non-scattered light interfering so as to form interference fringes behind the microscopic objects; and
an image sensor (995) positioned and configured to capture digital image frames by receiving the light propagated across the sample volume;
the computing arrangement (985) being connected to the measurement arrangement to receive image data (910, 920, 930) of the digital image frames.

10. An apparatus (900) as defined in claim 9, wherein the cuvette (991) is of flow-through type.

11. A computer program product comprising a non-transitory computer-readable medium that comprises computer-executable instructions which, when executed by one or more processors, cause the one or more processors to perform the method as defined in claim 1.

* * * * *